United States Patent [19]

House

[11] Patent Number: 4,524,223

[45] Date of Patent: Jun. 18, 1985

[54] RESOLUTION OF ALCOHOLS USING AMINO ACIDS

[75] Inventor: David W. House, Arlington Heights, Ill.

[73] Assignee: UOP Inc., Des Plaines, Ill.

[21] Appl. No.: 572,038

[22] Filed: Jan. 19, 1984

[51] Int. Cl.³ .................... C07C 29/92; C07C 67/48
[52] U.S. Cl. ..................................... 568/715; 560/20; 560/78; 568/810; 568/854; 568/877
[58] Field of Search ............. 568/715, 877, 810, 854; 560/20, 78

[56] References Cited

U.S. PATENT DOCUMENTS

| | | | |
|---|---|---|---|
| 3,109,018 | 10/1963 | Hanover | 568/715 |
| 3,305,591 | 2/1967 | Epstein et al. | 560/20 |
| 3,767,709 | 10/1973 | Fenton | 568/715 |
| 3,943,181 | 3/1976 | Fleischer et al. | 560/20 |
| 4,165,330 | 8/1979 | Whitney et al. | 568/715 |
| 4,386,205 | 5/1983 | Moore | 568/810 |
| 4,410,734 | 10/1983 | Martin et al. | 568/715 |

OTHER PUBLICATIONS

"Advances in Chromatography", vol. 16, pp. 177–183, (1978).
"Chem. Eng.", May 22, 1979, pp. 62–63.
Thanker et al., "J. Sci. Ind. Res. India", 21 B, 209–211, (1982).

*Primary Examiner*—Werren B. Lone
*Attorney, Agent, or Firm*—William H. Page, II; Eugene I. Snyder

[57] ABSTRACT

A general method of resolution of chiral alcohols is based on the relatively facile chromatographic resolution of their diastereomeric esters with optically active amino acids. The naturally occurring L-amino acids and D-(-)-phenylglycine are especially useful, and the method is applicable to a range of alcohols of diverse structure.

22 Claims, No Drawings

RESOLUTION OF ALCOHOLS USING AMINO ACIDS

This application relates to a general method of preparing an optically active alcohol from its racemic mixture. In particular, the invention disclosed herein relates to the resolution of a d,l-alcohol into its enantiomers via chromatographic separation of their diastereomeric esters with optically active amino acids and subsequent regeneration of the alcohol.

In many cases one enantiomer of an alcohol's racemic mixture exhibits the properties for which the alcohol finds utility. For example, l-menthol is the enantiomer enjoying commercial demand. Where an alcohol is physiologically active it often is found that activity resides largely, if not exclusively, in only one of its enantiomers.

A shortcoming of present syntheses of alcohols is that the product is racemic. The challenge is either to prepare optically active alcohol directly by a synthetic scheme utilizing a chiral environment, or to efficiently obtain the desired enantiomer from its racemate. Although substantial progress has been made in syntheses in a chiral environment, for example, use of chiral reagents, nonetheless the more usual way of preparing optically active material from inactive precursors is by direct or indirect separation of one or both of the components from a racemic mixture, i.e., the classical method of optical resolution.

One method of optical resolution infrequently used is the induction of a phase change in a chiral environment, thereby causing a preferential phase change in but one of the enantiomers of a racemate. This principle is employed in U.S. Pat. No. 3,943,181 where a supersaturated solution of an ester of racemic menthol with benzoic acid, a substituted benzoic acid, or cyclohexanecarboxylic acid is seeded with crystals of the l-menthyl ester, thereby causing preferential precipitation of the l-menthyl ester. Although elegant in its simplicity, the method demands stringent temperature control to within about 0.01° C. (Chem. Eng., May 22, 1979, pp. 62–3).

Other methods of optical resolution utilize the different physical properties of diastereomers to purify at least one diastereomer by some conventional separation method. The desired enantiomer is then obtained from the purified diastereomer by an appropriate chemical conversion. Fractional or selected crystallization commonly is employed as the method of separating diastereomers. For example, in U.S. Pat. No. 3,109,018 the hydrogen phthalate ester of racemic menthol is reacted with 0.5 mole of optically active 1-(1-naphthyl)-ethylamine and 1 mole of ammonia in an organic solvent to afford diastereomeric salts whose solubility in water differs drastically, thereby permitting the isolation and purification of one of the diastereomers. Subsequent acid treatment of the purified diastereomer affords the hydrogen phthalate ester which is subsequently hydrolyzed to afford l-menthol. An interesting resolution of menthol is described in U.S. Pat. No. 3,305,591 where a solution of the racemate, preferably containing acid, is contacted under interesterification conditions with an insoluble, cross-linked, optically active polymer containing ester groups and acting as the solid phase under chromatographic conditions. Presumably the process involves reversible diastereomer formation under dynamic equilibrium conditions, thereby effecting separation as the enantiomers are eluted from the column. Although this process is one where resolution via chromatoraphic separation of a racemate is achieved by a chiral stationary phase, the more usual process is chromatographic separation of diastereomers by an achiral stationary phase, as described, for example, in "Advances in Chromatography," Vol. 16, pp. 177–83 (1978).

For a chromatographic separation of diastereomers to be commercially successful as a method of resolving alcohols, stringent requirements are placed on the diastereomers. One requirement is that the optically active alcohol must be regenerable in high chemical and optical yield. Another requirement is that the diastereomers be readily separable on a wide variety of stationary phases using a diversity of eluants, so that the method itself is relatively insensitive to changes in supply and quality of materials, and is relatively undemanding in process control. A basic observation which acts as a foundation for this invention is that diastereomeric esters of certain optically active amino acids and racemic alcohols are readily separable under a broad diversity of chromatographic conditions. Since the optically active enantiomers of the alcohol may be readily regenerated from the separate diastereomers by various means in high chemical and stereochemical yield and purity, the aforementioned observation provides the basis for a method of resolving alcohols of great structural variety. Additionally, the optically active amino acid also can be recovered in high yield to be reused in other cycles of diastereomer preparation, separation, and enantiomeric alcohol regeneration.

SUMMARY OF THE INVENTION

An object of this invention is to obtain an optically active alcohol from its racemate. An embodiment is a process comprising the chromatographic separation of the diastereomeric esters of a racemic alcohol with an optically active amino acid, liberating the optically active alcohol from a purified diastereomer, and recovering the alcohol regenerated thereby. In a more specific embodiment, the amino acids are naturally occurring amino acids. In a still more specific embodiment the naturally occurring amino acids have the L-configuration. In yet another embodiment the amino acid is l-phenylglycine.

DESCRIPTION OF THE INVENTION

The invention described herein is a method of obtaining a purified diastereomer from which an optically active alcohol may be readily regenerated comprising contacting a solution of the diastereomeric esters from a racemic alcohol and an optically active amino acid with a chromatographic support, eluting the support with a solvent under chromatographic conditions, and collecting at least one effluent fraction containing a purified diastereomer. In another aspect the invention herein is a method of preparing an optically active alcohol by treating the purified diastereomer to liberate the optically active alcohol, and recovering the alcohol. This invention is made possible by the observation that the diastereomeric esters of alcohols and certain amino acids are easily separated on a variety of chromatographic supports with a diversity of solvents as eluants.

Diastereomers are compounds with at least two chiral centers, at least one of which is different and at least one of which is the same. In the case where the diastereomers contain two chiral centers, there are two sets of diastereomers, each set being composed of two enantiomers. The members of each diastereomeric set differ in that one chiral center is the same and the other center is different. For example, where A represents an amino acid, M represents an alcohol with one chiral center, and the notations d and l represent rotations of polarized light, the diastereomeric sets of the esters of an alcohol with amino acids are,

| (1) l-M-d-A | (3) l-M-l-A |
|---|---|
| (2) d-M-l-A | (4) d-M-d-A | where (1) and (2) are enantiomers, as are (3) and (4), but both (1) and (2) are diastereomers of both (3) and (4). In particular, (2) and (3) are the diastereomeric esters of a racemic alcohol and l-amino acids.

The diastereomeric esters used in this invention are readily separable by chromatography on a broad diversity of chromatographic supports using a broad range of solvents as eluants. Column selectivity can be defined by the quantity, $$\alpha = \frac{(t_2 - t)}{(t_1 - t)}$$

where $t_2$ and $t_1$ are the retention times of the two diastereomers and t is the retention time of unretained components. This column selectivity, alpha, is a measure of the ease of separation of components on a particular support and with a particular solvent as eluant. Increasing values of alpha represent increasing ease of separation. Values of alpha greater than about 1.3 imply that the separation is quite facile; values of alpha from about 1.05 to about 1.3 imply that the separation is feasible although not necessarily facile. The diastereomers of racemic alcohols used in this invention may have alpha values even greater than about 1.5.

The diastereomers used in this invention are esters from racemic alcohols and amino acids, especially alpha-amino acids. Among the amino acids of this invention are the naturally occurring amino acids, such as alanine, arginine, asparagine, aspartic acid, cysteine, cystine, 3,5-dibromotyrosine, 3,5-diiodotyrosine, glutamic acid, glutamine, histidine, hydroxylysine, hydroxyproline, isoleucine, leucine, lysine, methionine, phenylalanine, proline, serine, threonine, thyroxine, tryptophane, tyrosine, and valine. In particular, the naturally occurring amino acids, which have the L-configuration, are especially desired in the practice of this invention. However desirable the natural amino acids may be, other amino acids also can be utilized advantageously, such as phenylglycine, nuclear substituted derivatives of phenylglycine such as 4-hydroxyphenylglycine, meta-tyrosine, 3,4-dihydroxyphenylalanine, and 3,5-diiodothyronine, with D-(-)-phenylglycine being particularly preferred.

The alcohols which may be successfully resolved by my invention are susceptible to rather large structural variations. One class of alcohols is represented by the formula,

Ar is a monovalent radical whose parent is selected from the group consisting of benzene, naphthalene, anthracene, phenanthrene, and chrysene, with alcohols where Ar is a phenyl group being especially favored. The moiety R may be an alkyl, alkenyl, or alkynyl moiety, generally containing up to about 20 carbon atoms, and even more often containing from 1 to about 10 carbon atoms. R also may be a cycloalkyl or cycloalkenyl moiety of ring size from 3 to about 10 atoms, most often from 5 to about 8 atoms, with the cyclopentyl and cyclohexyl moieties being particularly preferred. R also may represent the class formed by haloalkyl, especially fluoroalkyl and perhaloalkyl, moieties containing up to about 20 carbon atoms, especially from 1 to about 10 carbons. Examples of R include methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, fluoromethyl, chloromethyl, bromomethyl, iodomethyl, difluoromethyl, dichloromethyl, dibromomethyl, diiodomethyl, trifluoromethyl, trichloromethyl, etc., perfluoroethyl, perchloroethyl, perbromoethyl, perfluoropropyl, perfluorobutyl, and so on, cyclopropyl, cyclobutyl, cyclopentyl, cyclohexyl, cycloheptyl, cyclooctyl, cyclononyl, and cyclodecyl, and their unsaturated counterparts, the alkenyl, alkynyl, and cycloalkenyl analogues.

It is to be clearly understood that Ar and R also may bear substitutents otherwise inert under conditions of diastereomer formation, chromatographic separation, and alcohol regeneration. For example, Ar and cycloalkyl may bear one or more halogens, alkoxy, nitro, or cyano moieties, and in particular may have alkyl substituents. Where R is an alkyl, alkenyl, or alkynyl moiety it may be aryl substituted, or have one or more alkoxy, nitro, cyano, etc., substituents.

Another class of alcohols is represented by the formula

That R, R' be different is a prerequisite for chirality. Both R and R' are alkyl, alkenyl, alkynyl, haloalkyl, cycloalkyl, or cycloalkenyl moieties conforming to the description given above. Generally, it is necessary that R' be bulkier than R to achieve a satisfactory separation of diastereomers by my invention, i.e., R' must have substantially greater steric requirements than does R. This is frequently the case when R is a primary alkyl moiety and R' is a secondary or tertiary alkyl moiety. Substantial steric differences also may result when R is a linear alkyl, alkenyl, or alkynyl moiety and R' has one or more branched carbon atoms.

Yet another class of alcohols encompasses those having the bicyclo [2.2.1] heptane or bicyclo [2.2.2] octane skeletal system, and their unsaturated analogues. Examples include bicyclo [2.2.1] heptan-1-ol, bicyclo [2.2.1] heptan-2-ol, bicyclo [2.2.1] heptan-7-ol, bicyclo [2.2.1] hept-5-en-2-ol, 1-methyl-bicyclo [2.2.1] heptan-2-ol, 5-methyl-bicyclo [2.2.1]-heptan- 2-ol, 6-ethyl-bicyclo [2.2.1] heptan-2-ol, 7-chloro-bicyclo [2.2.1] heptan-2-ol, 3,5-dimethylbicyclo [2.2.2] octan-2-ol, 5,6-dibromobicyclo [2.2.2] octan-2-ol, and so forth.

A solution of the diastereomeric esters is contacted with a chromatographic support, with a broad range of supports usable in the practice of this invention. One group of preferred supports is represented by silica, alumina, and the zeolites. Another group of supports consists of supports commonly used for reverse phase chromatography. Reverse phase chromatography is that branch of chromatography where the mobile phase is more polar than the stationary phase, or support. Among the supports which are used in reverse phase chromatography are silicas modified by silanization so as to bear nonpolar groups on the surface of the silica as replacements for surface hydroxyl groups. For example, such silicas may bear long-chain alkyl, aryl, amino, or cyano groups bonded to the surface via a silicon-bearing moiety.

The chromatographic support is eluted with a solvent or solvent system under chromatographic conditions. By "chromatographic conditions" are meant those general principles of separation by chromatography known to those skilled in the art and routinely applied to a liquid-solid chromatographic operation. Thus, for example, solvent flow is uniform, formation of gas bubbles is avoided, disturbance of the solid support is minimized, and so forth. The solvents which may be used in the process of this invention are those typical of chromatographic processes. Among suitable solvents are aliphatic hydrocarbons such as pentane, hexane, heptane, octane, nonane, decane, cyclopentane, cyclohexane, diisobutylene, pentene, hexene, etc.; aromatic hydrocarbons such as benzene, toluene, the xylenes, ethylbenzene, diethylbenzene, methylethylbenzene and the like; halogenated hydrocarbons, especially chlorinated and fluorinated hydrocarbons illustrated by chloroform, methylene chloride, carbon tetrachloride, chloropropane, chlorobutane, chloropentane, fluoralkanes, bromoethane, chlorobenzene, chlorotoluene, and ethylene chloride; sulfides, especially carbon disulfide; ethers as illustrated by diethyl ether, tetrahydrofuran, tetrahydropyran, and dioxane; esters, especially acetates, such as methyl acetate, butyl acetate, and esters of saturated carboxylic acids up to about 6 carbon atoms where the portion arising from the alcohol is saturated and contains up to about 6 carbon atoms; ketones containing up to about 8 carbon atoms, such as acetone, butanone, pentanone, hexanone, heptanone, and octanone; nitroalkanes such as nitromethane, nitroethane, nitropropane, and nitrobutane; amines, especially pyridine; nitriles, such as acetonitrile, propionitrile, and butyronitrile; alcohols containing up to about 8 carbon atoms, including diols and triols; acetic acid and dimethylsulfoxide.

At least one effluent fraction is collected containing a purified diastereomer. Often the effluent is monitored for a particular property to determine suitable effluent fractions. For example, it may be monitored for a particular ultraviolet or infrared absorbance or for its refractive index, as representative of properties used to determine effluent fractions. Because the concentration of purified diastereomer may be low, differential measurements are especially valuable in determining effluent fractions.

After the effluent fraction or fractions containing a purified diastereomer is/are collected, the purified diastereomer is treated to regenerate the now optically active alcohol. Suitable methods of treating the purified diastereomer to afford optically active alcohol include hydrolysis, alcoholysis, aminolysis, and reduction. Hydrolysis generally will be catalyzed either by acid or base, with base catalysis being somewhat preferred to preserve the maximum optical purity of the liberated alcohol as well as that of the liberated amino acid. Hydrolysis is a preferred treatment because the amino acid formed concurrently can be readily recovered for reuse in a cyclic process. Mineral acids exemplify suitable acid catalysts; alkali metal hydroxide and carbonates exemplify suitable base catalysts.

Alcoholysis is the process whereby the alcoholic portion of the diastereomeric ester is replaced by another alcohol, and represents transesterification where the alcohol portion of an ester is metathesized. Alcoholysis also is acid and base catalyzed, with base catalysis being preferred. Aminolysis is the process whereby the alcoholic portion of the diastereomeric ester is replaced by an amine or ammonia. Such a process generally is self-catalyzed because of the nucleophilicity of the amine or ammonia used. Reduction represents another method of liberating an optically active alcohol from the purified diastereomer. In this treatment the carboxyl portion of the ester is reduced to a hydroxymethyl group to afford the original alcohol, albeit optically active, and an alcohol derived from the amino acid portion of the ester. Reduction may be catalytic, using for example copper chromite as a catalyst, or it may be effected by chemical reducing agents such as lithium aluminum hydride, other aluminohydrides, lithium borohydride, and so on, to cite but a few examples.

It will be recognized by the skilled worker that there is a multitude of methods available in his arsenal for liberating an optically active alcohol from a purified diastereomer. It is to be emphasized that the particular method chosen is not critical; choices generally will be dictated by a desire to maximize chemical and optical yield while minimizing cost. It also is to be emphasized that the particular method used is incidental to the practice of my invention, as contrasted with being an essential part thereof. Regardless how the optically active alcohol is liberated, it is then recovered by suitable means, as for example by crystallization, distillation, etc.

The following examples merely illustrate this invention and are not intended to limit it in any way.

The chromatographic system employed in these examples was composed of a pump capable of flow rates up to 10 ml per minute at 10,000 psi, a septumless injector equipped with zero dead volume fittings, the appropriate column for separation, a dual-channel absorbance detector equipped for monitoring effluent at 254 and 280 nm, and a dual-channel recorder. All tubing used was stainless steel of 1/16" outside diameter with 0.009" inside diameter. The columns were of stainless steel, 4.6 mm inside diameter and 25 cm long.

All solvents used as eluants were degassed and filtered before use. The hexane was freshly distilled and the forward phase eluants were dried using anhydrous magnesium sulfate. All eluants and other chemicals described were obtained from commercial sources and used without further purification.

EXAMPLE 1

Resolution of 1-Phenylethanol

To a 50-ml single-neck, round-bottomed flask fitted with a Dean-Stark trap and reflux condenser and containing a Teflon-coated magnetic stirring bar were added D-(-)-phenylglycine (0.25 g, 1.65 mmol), p-toluenesulfonic acid (0.36 g, 1.89 mmol), 5 ml of (d,l)-1-phenylethanol, and 5 ml of a 70:30 mixture of benzene and toluene. The solution was heated at reflux for about 16 hours, after which liquid was removed by heating the mixture in vacuo. The (d,l)-1-phenylethyl ester of D-(-)-phenylglycine was obtained in about 35%.

A sample of the diastereomeric esters was injected onto a silica gel column and eluted using hexane as the solvent at a pressure of 410 psig and a flow of 1 ml per minute, with effluent monitored by ultraviolet absorbance at 254 and 280 nm. The individual diastereomeric esters were eluted at column volumes of 4.99 and 5.34, for an alpha value of 1.07.

Each of the eluant fractions may be collected, solvent may be removed by evaporation to afford the two purified diastereomeric esters, and each of the purified diastereomers may be hydrolyzed with base to afford, separately, both (d)- and (l)-1-phenylethanol.

EXAMPLE 2

Resolution of Borneol

To 30 ml of a 70:30 benzene:toluene mixture in a 100-ml single-neck, round-bottomed flask fitted with a Dean-Stark trap and reflux condenser and containing a Teflon-coated magnetic stirring bar were added D-(-)-phenylglycine (3.00 g, 20 mmol), d,l-borneol (3.06 g, 20 mmol), and p-toluenesulfonic acid (3.78 g, 20 mmol). The mixture was stirred magnetically at reflux for several days without achieving homogeneity. The cooled reaction mixture was washed with aqueous bicarbonate, the organic phase was filtered, and the filtrate was dried with anhydrous magnesium sulfate to afford a solution containing the diastereomeric esters of (d,l)-bornyl D-(-)-phenylglycine (ca. 10% yield).

The diastereomeric esters prepared above were separated on a 10μ silica gel column using 20% isopropyl alcohol in hexane as the eluant. The effluent was monitored by ultraviolet absorbance at 254 nm, with an alpha value of 1.07 again being observed.

The individual enantiomeric borneols may be obtained by separately hydrolyzing each of the purified diastereomeric esters in basic solution.

What is claimed is:

1. A method of obtaining a purified diastereomer from which an optically active alcohol may be readily regenerated comprising contacting a solution containing the diastereomeric esters of an optically active amino acid selected from the group consisting of naturally occurring amino acids, phenylglycine, 4-hydroxyphenylglycine, meta-tyrosine, 3,4-dihydroxyalanine, and 3,5-diiodothyronine, and a racemic alcohol selected from the group consisting of benzylic alcohols whose formula is

ArCHOH, where
Ar is a monovalent radical whose parent is selected from the group consisting of benzene, naphthalene, anthracene, phenanthrene, and chrysene, and
R is an alkyl, alkenyl, alkynyl, haloalkyl, or cycloalkyl moiety,
other secondary alcohols whose formula is

R'CHOH, where
R is an alkyl or cycloalkyl moiety,
R' is an alkyl, alkenyl, alkynyl, haloalkyl, or cycloalkyl moiety,
R' is different from R, and
R' is sterically bulkier than R,
and bicyclo [2.2.1] heptyl or bicyclo [2.2.2] octyl alcohols, with a chromatographic support, eluting said support with a solvent under chromatographic conditions, and collecting at least one effluent fraction containing a purified diastereomer of said ester.

2. The method of claim 1 where the naturally occurring amino acid is selected from the group consisting of alanine, arginine, asparagine, aspartic acid, cysteine, cystine, 3,5-dibromotyrosine, 3,5-diiodotyrosine, glutamic acid, glutamine, histidine, hydroxylysine, hydroxyproline, isoleucine, leucine, lysine, methionine, phenylalanine, proline, serine, threonine, thyroxine, tryptophane, tyrosine, and valine.

3. The method of claim 2 where the amino acids have the L-configuration.

4. The method of claim 1 where the amino acid is D-(-)-phenylglycine.

5. The method of claim 1 where the alcohol has the formula

ArCHOH, where Ar is a phenyl group and R is an alkyl, haloalkyl, or cycloalkyl moiety containing up to about 20 carbon atoms.

6. The method of claim 5 where the alkyl or cycloalkyl moiety contains up to about 10 carbon atoms.

7. The method of claim 1 where the alcohol has the formula

R'CHOH where R is a primary alkyl, or haloalkyl moiety and R' is secondary or tertiary alkyl, haloalkyl, or cycloalkyl moiety, and both R and R' contain up to about 20 carbon atoms.

8. The method of claim 7 where both R and R' contain up to about 10 carbon atoms.

9. The method of claim 8 where the alcohol is 1-phenylethanol.

10. The method of claim 1 where the alcohol is borneol.

11. The method of claim 1 where the chromatographic support is selected from the group consisting of silica, alumina, modified silicas and the zeolites.

12. A method of obtaining an optically active alcohol comprising contacting a solution containing the diastereomeric esters of an optically active amino acid selected from the group consisting of naturally occurring amino acids, phenylglycine, 4-hydroxyphenylglycine, meta-tyrosine, 3,4-dihydroxyalanine, and 3,5-diiodothyronine, and a racemic alcohol selected from the group consisting of benzylic alcohols whose formula is

ArCHOH, where
Ar is a monovalent radical whose parent is selected from the group consisting of benzene, naphthalene, anthracene, phenanthrene, and chrysene, and R is an alkyl, alkenyl, alkynyl, haloalkyl or cycloalkyl moiety, other secondary alcohols whose formula is

where
- R is an alkyl or cycloalkyl moiety,
- R' is an alkyl, alkenyl, alkynyl, haloalkyl, or cycloalkyl moiety,
- R' is different from R, and
- R' is sterically bulkier than R, and bicyclo [2.2.1] heptyl or bicyclo [2.2.2] octyl alcohols, with a chromatographic support, eluting said support with a solvent under chromatographic conditions, collecting at least one effluent fraction containing a purified diastereomer of said ester, treating the purified diastereomer to regenerate the alcohol, and recovering the optically active alcohol formed thereby.

13. The method of claim 12 where the naturally occurring amino acid is selected from the group consisting of alanine, arginine, asparagine, aspartic acid, cysteine, cystine, 3,5-dibromotyrosine, 3,5-diiodotyrosine, glutamic acid, glutamine, histidine, hydroxylysine, hydroxyproline, isoleucine, leucine, lysine, methionine, phenylalanine, proline, serine, threonine, thyroxine, tryptophane, tyrosine, and valine.

14. The method of claim 13 where the amino acids have the L-configuration.

15. The method of claim 12 where the amino acid is D-(-)-phenylglycine.

16. The method of claim 12 where the alcohol has the formula

where Ar is a phenyl group and R is an alkyl, haloalkyl, or cycloalkyl moiety containing up to about 20 carbon atoms.

17. The method of claim 16 where the alkyl or cycloalkyl moiety contains up to about 10 carbon atoms.

18. The method of claim 12 where the alcohol has the formula

where R is a primary alkyl or haloalkyl moiety and R' is a secondary or tertiary alkyl, haloalkyl, or cycloalkyl moiety, and both R and R' contain up to about 20 carbon atoms.

19. The method of claim 18 where both R and R' contain up to about 10 carbon atoms.

20. The method of claim 18 where the alcohol is 1-phenylethanol.

21. The method of claim 12 where the alcohol is borneol.

22. The method of claim 12 where the chromatographic support is selected from the group consisting of silica, alumina, modified silicas and the zeolites.

* * * * *